United States Patent [19]
Robbins et al.

[11] Patent Number: 5,660,892
[45] Date of Patent: Aug. 26, 1997

[54] METHOD OF FORMING A METALLIC FILM

[75] Inventors: William B. Robbins, Maplewood; Leif Christensen, St. Paul; Richard E. Volkmann, Arden Hills; Rafael M. Yasis, White Bear Lake; Laura M. Aguilar, St. Paul, all of Minn.

[73] Assignee: Minnesota Mining and Manufacturing Company, St. Paul, Minn.

[21] Appl. No.: 569,713

[22] Filed: Dec. 8, 1995

Related U.S. Application Data

[62] Division of Ser. No. 62,390, May 14, 1993, Pat. No. 5,506,059.

[51] Int. Cl.$^6$ ...................................... H05H 1/00
[52] U.S. Cl. .................. 427/537; 427/250; 427/255.4; 427/255.7; 427/258; 427/333; 427/343; 427/383.1; 427/404; 427/430.1; 427/576; 427/123
[58] Field of Search .................. 427/537, 576, 427/250, 255.4, 255.7, 758, 333, 343, 383.1, 404, 430.1; 437/180.2

[56] References Cited

U.S. PATENT DOCUMENTS

| | | | |
|---|---|---|---|
| Re. 31,454 | 12/1983 | Hymes | 128/641 |
| 1,662,446 | 3/1928 | Wappler | 128/798 |
| 3,255,099 | 6/1966 | Wolinski | 204/169 |
| 3,330,681 | 7/1967 | Scharf et al. | 117/33.3 |
| 3,940,533 | 2/1976 | Arsac | 428/225 |

(List continued on next page.)

FOREIGN PATENT DOCUMENTS

| | | |
|---|---|---|
| 1011002 | 5/1977 | Canada . |
| 0 348 062 A1 | 12/1989 | European Pat. Off. . |
| 61-59526 | 12/1986 | Japan . |
| WO92/15723 | 9/1992 | WIPO . |
| WO93/19218 | 9/1993 | WIPO . |

OTHER PUBLICATIONS

75–Crystallogr. Liquid Crystals, vol. 106, (1987) No. 225070 providing an abastract for Jap. Patent Publication 61–59,526 (no month avail.).

DATABASE WPI, Section Ch, Week 8720, Derwent Publications Ltd. London, GB; Class A35, and 87–139233 & JP, A 62 077 453 9TEIJIN KK), Apr. 9, 1987.

Patent Abstractsd Of Japan, vol. 013, No. 569 (C–666), Dec. 15, 1989.

*Primary Examiner*—Bernard Pianalto
*Attorney, Agent, or Firm*—Gary L. Griswold; Walter N. Kirn; John H. Hornickel

[57] ABSTRACT

A metallic film is disclosed. The film has a layer of an organic polymer substrate having an sulfur-reactive surface, to which is adhered a vapor deposited metallic layer. Optionally, a metallic halide layer is formed on the metallic layer to provide depolarizing capacity for the metallic film. Methods of making and using the metallic film are disclosed. Biomedical electrodes, including radiolucent defibrillation electrodes, window films, optical reflectors, and flexible electronic circuits are articles which can use the metallic film as a component.

11 Claims, 2 Drawing Sheets

U.S. PATENT DOCUMENTS

| | | | |
|---|---|---|---|
| 3,960,141 | 6/1976 | Bolduc | 128/2.06 E |
| 3,981,691 | 9/1976 | Cuneo | 29/195 |
| 4,039,714 | 8/1977 | Roubal et al. | 428/336 |
| 4,052,368 | 10/1977 | Larson | 260/75 S |
| 4,123,280 | 10/1978 | Malinovaki et al. | 96/94 BF |
| 4,257,414 | 3/1981 | Cartmell | 128/641 |
| 4,307,150 | 12/1981 | Roche | 428/336 |
| 4,391,278 | 7/1983 | Cahalan et al. | 128/640 |
| 4,452,679 | 6/1984 | Dunn et al. | 204/164 |
| 4,493,872 | 1/1985 | Funderburk et al. | 428/332 |
| 4,524,087 | 6/1985 | Engel | 427/2 |
| 4,539,996 | 9/1985 | Engel | 125/640 |
| 4,554,924 | 11/1985 | Engel | 128/640 |
| 4,645,714 | 2/1987 | Roche et al. | 428/458 |
| 4,715,382 | 12/1987 | Strand | 128/640 |
| 4,735,996 | 4/1988 | Nagal et al. | 525/326.4 |
| 4,759,971 | 7/1988 | Weissberger et al. | 428/215 |
| 4,771,783 | 9/1988 | Roberts | 128/640 |
| 4,821,363 | 4/1989 | Bell et al. | 428/420 |
| 4,822,451 | 4/1989 | Ouderkirk et al. | 156/643 |
| 4,846,185 | 7/1989 | Carim | 128/641 |
| 4,848,345 | 7/1989 | Zenkich | 128/419 D |
| 4,848,348 | 7/1989 | Craighead | 128/639 |
| 4,848,353 | 7/1989 | Engel | 128/640 |
| 4,879,176 | 11/1989 | Ouderkirk et al. | 428/323 |
| 4,886,681 | 12/1989 | Clabes et al. | 427/38 |
| 4,895,169 | 1/1990 | Health | 128/798 |
| 4,974,917 | 12/1990 | Kornerup | 128/798 |
| 5,012,810 | 5/1991 | Strand et al. | 128/640 |
| 5,019,415 | 5/1991 | Oehr et al. | 427/39 |
| 5,133,356 | 7/1992 | Bryan et al. | 128/640 |
| 5,150,708 | 9/1992 | Brooks | 128/419 D |
| 5,178,965 | 1/1993 | Miyamoto et al. | 428/463 |
| 5,200,272 | 4/1993 | Sirinyan et al. | 428/458 |
| 5,275,882 | 1/1994 | Conley | 428/336 |
| 5,279,899 | 1/1994 | Asrar | 428/458 |

METHOD OF FORMING A METALLIC FILM

This is a division of application Ser. No. 08/062,390 filed May 14, 1993 U.S. Pat. No. 5,506,059.

FIELD OF THE INVENTION

This invention relates to metallic films and articles using such metallic films to advantage.

BACKGROUND OF THE INVENTION

U.S. Pat. No. 4,257,424 (Cartmell) discloses that the use of a vacuum deposition of silver proves to be undesirable because vacuum deposited silver is not securely retained by a substrate such as Mylar.

U.S. Pat. No. 4,848,348 (Craighead) discloses the deposition of silver on a primed surface of an organic film. The primer is comprised of binder and powder particles, which was preferred to using a plasma treated film.

U.S. Pat. No. 3,255,099 (Wolinski) discloses the use of corona treatment at atmospheric pressure as a priming method for organic films. Among inorganic agents used is hydrogen sulfide.

Japanese Patent Publication 61-59,526 discloses the deposition of $H_2S$ at a 200 Angstrom thickness on a surface.

SUMMARY OF THE INVENTION

The present invention overcomes the disadvantages of the prior art by providing a metallic film comprising a substrate of organic polymer, a sulfur-reactive surface on the organic polymer substrate, and a metallic layer adhered to the organic polymer surface via sulfur-metal interaction.

"Sulfur-reactive surface" means that the surface of the organic polymer substrate has become reactive due to the presence of a composition having a sulfur functionality.

One embodiment of the present invention is use of a sulfur-containing compound, e.g., barium sulfate, in the bulk of the organic polymer substrate, such that a metallic layer is adhered to the surface of the organic polymer substrate with greater adhesion than such adhesion in the absence of such sulfur-containing compound.

Another embodiment of the present invention is the use of a sulfur-containing compound, e.g., hydrogen sulfide reacting with the surface of the organic polymer substrate to provide the surface with that sulfur functionality.

A third embodiment of the present invention is the use of sulfonated organic polymer substrate surface, i.e., sulfonated polyester.

"Sulfur-metal interaction" means covalent bonding or coordination bonding, or a combination of both, depending on the type of composition having sulfur functionality and the type of metallic layer employed.

The presence of the sulfur functionality on the organic polymer substrate is used according to the present invention to improve adhesion of a metal, e.g., silver, to the substrate.

According to the first embodiment of the present invention, the organic polymer substrate is modified by mixing into such polymer, during or after formation, a sulfur-containing compound which is reactive with a metal when the metal contacts surfaces of the substrate during vapor deposition thereof.

According to the second embodiment of the present invention, the organic polymer substrate is modified by exposure of the surface(s) of the substrate to a vacuum glow discharge or plasma. The gas in which this plasma is created comprises a sulfur-containing compound. The reaction between the organic polymer and the plasma-delivered sulfur-containing compound produces an organic-sulfur surface having carbon-sulfur covalent bonds.

The sulfur-reactive surface is a priming surface for reaction of a metal to adhere to such primed surface via metal-sulfur interaction.

A feature of the invention is the ease and permanence of formation of a metallic film using a sulfur-reactive surface, primed for metal-sulfur interaction with a vapor deposited metal.

Another feature of the invention is the use of an sulfur-reactive surface to form a coordination or covalent bond with the metal layer, such as silver.

An additional feature of the invention is ability to form an extremely thin, vapor-coated, precious metallic layer on an organic polymer substrate having acceptable or superior functional properties. This ability can minimize expense in production of metallic films when using precious metals to form films.

An advantage of the invention is the elimination of the use of a metallic ink in the formation of a metallic film. An ink is dependent on metallic particle size, proper binder selection and usage, and often requires high coating weights to achieve acceptable conductivity. Hence, a metallic ink having an excessively high coating weight yields a metallic film which is excessively radio-opaque for biomedical electrode usages during medical imaging procedures.

Another advantage of the invention is the use of simple, unfabricated metallic stock, such as metal pellets, that can be vaporized for application to the sulfur-reactive primed surface of an organic polymer substrate. Vacuum deposition of such metal assures a very thin uniform surface to establish acceptably high conductivity and minimize radio-opacity to achieve at least radiolucency and possibly radiotransparency. Also, use of vacuum deposition of metal optimizes purity of the metallic coating.

Another advantage of the present invention is that the priming of organic polymer substrates minimizes delamination of metal from the film and reduces corrosion. In the embodiments of the present invention, it has been found that using the sulfur-reactive surfaces of the present invention to vapor deposit metals achieves such adhesion that cohesive failure of the organic polymer substantially occurs prior to adhesive failure of the metallic layer to the organic polymer substrate.

Another advantage of the present invention is the minimal use of expensive conductive metals, such as silver, without compromising conductivity of the metallic film so made.

The present invention also comprises a biomedical electrode comprising an electrical conductor, a field of ionically conductive medium having an area with a perimeter contacting the electrical conductor to define an edge, and a layer of non-conductive material contacting the field of ionically conductive medium and the electrical conductor and having an opening through which the field of ionically conductive medium is exposed, wherein the layer of non-conductive material covers the perimeter of the ionically conductive medium and the edge.

For a greater appreciation of the invention, embodiments of the invention are described after a brief description of the drawing.

EMBODIMENTS OF THE INVENTION

Organic Polymer Substrate

Organic polymers useful as substrates are those which can be fabricated in the form of thin films for a variety of metallic film usages. Nonlimiting examples of organic polymers are polyolefins, polyesters, fluorinated polyolefins (e.g., polytetrafluoroethylene), and polycarbonates. If using more fully, fluorinated polyolefins, a pre-treatment to remove at least some fluorination is necessary. Among these organic polymers, polyesters are preferred for their known utility. Among polyesters, polyethylene terephthalates are most preferred.

The organic polymer can have any thickness acceptable to the ultimate usage.

For use as conductors in biomedical electrodes, the thickness of the organic polymer as the substrate ranges from about 6 µm to about 500 µm. Desirably, the thickness ranges from about 25 µm to about 250 µm. Preferably, the thickness ranges from about 25 µm to about 175 µm.

For use as window films, the substrate thickness ranges from about 4 µm to about 600 µm. Desirably, the thickness ranges from about 20 µm to about 250 µm. Preferably, the thickness ranges from about 25 µm to about 175 µm.

For use as optical reflectors, the substrate thickness ranges from about 4 µm to about 600 µm. Desirably, the thickness ranges from about 20 µm to about 250 µm. Preferably, the thickness ranges from about 25 µm to about 175 µm.

For use in flex circuitry, the substrate thickness ranges from about 4 µm to about 600 µm. Desirably, the thickness ranges from about 20 µm to about 250 µm. Preferably, the thickness ranges from about 20 µm to about 200 µm.

Optionally, the organic polymer substrate can be prepared for sulfur priming by employing the technique known as flashlamp treatment, such as that disclosed in U.S. Pat. Nos. 4,822,451 and 4,879,176 (both Ouderkirk et al.), for use with semicrystalline polymers, the disclosures of which are incorporated by reference. Flashlamp treatment is known to provide an quasi-amorphous microsurface on a polyester substrate. Preferably, the organic polymer substrate can undergo the flashlamp treatment under conditions disclosed in the patents identified above in order to better prepare the surface of the organic polymer substrate for plasma generation of the sulfur-reactive surface, with enhanced adhesion, according to the second embodiment of the present invention.

Sulfur-reactive Surface

In the first embodiment of the present invention, it is known that the mixture of a sulfur-containing compound into the bulk of an organic polymer substrate as a filler improves cohesive strength of, or provides opacity for, the polymer composite. Unexpectedly, such sulfur-containing compound also provides an adhesion of the metallic layer that is superior to the adhesion provided by a polymer substrate without such sulfur-containing compound mixed therein.

The mechanism of such increased adhesion is not completely known. Without being limited to a particular theory, it is believed that the sulfur-containing compound provides a sulfur-reactive surface to which metal can adhere using metal-sulfur interaction.

Organic polymers having sulfur-containing compounds are commercially available, such as ICI 329 and ICI 339 "Melinex" branded polyester films commercially available from ICI Americas of Hopewell, Va., that contain barium sulfate as a filler therein.

In the second embodiment of the present invention, the surface of the organic polymer substrate, (preferably rendered quasi-amorphous using a flashlamp treatment), is primed with a sulfur-containing compound to produce an organosulfur surface.

The organosulfur surface is formed by a plasma-induced reaction of the organic polymer with a sulfur-containing gas or vapor. Nonlimiting examples of sulfur-containing compounds are alkyl mercaptans, hydroxyalkyl mercaptans, hydrogen sulfide, alkyl sulfides, carbon disulfide, and other sulfide gases. Preferably, the sulfur-containing compound is hydrogen sulfide gas.

The sulfur-containing compound is reacted with the organic polymer surface using a vacuum glow discharge or plasma in a chamber at pressures significantly below atmospheric pressures, unlike those reaction conditions employed in corona treatment techniques. The reaction between the organic polymer surface and the sulfur-containing gas or vapor in the plasma produces an organosulfur surface having carbon-sulfur covalent bonds. Thus, an organosulfur surface is uniformly formed as a primer surface for reaction with metal according to the present invention.

In the third embodiment of the present invention, a sulfonated surface layer can be prepared by flood coating an aqueous dispersion on an organic polymer substrate according to techniques known to those skilled in the art. Such techniques are described in U.S. Pat. No. 4,052,368 (Larson), the disclosure of which is incorporated by reference herein. A commercially available polymer having a sulfonated surface is "Hoechst" SA polyester film from Hoechst Chemicals.

The sulfur-reactive surface is thin, but can be controlled depending on the type of surface provided and the embodiment of the invention employed. The sulfur-reactive surface can be continuous or discontinuous, depending on the thickness of the sulfur-reactive surface and depending on the embodiment of the invention employed.

When using the first embodiment of the present invention, the presence of sulfur-containing compound in the bulk of the organic polymer provides sulfur functionality at the surface of the substrate. The surface is discontinuous due to the particulate nature of the sulfur-containing compound in the bulk of the organic polymer substrate.

When using the second embodiment of the present invention, the surface modified by sulfur functionality is preferably on the order of a few nanometers thick. The surface can be continuous or discontinuous. As measured by XPS (ESCA), the organosulfur surface formed in situ at the surface of the organic polymer ranges from a submonolayer which is discontinuous to a continuous layer of about 10 nm. Desirably, the surface modified by sulfur functionality ranges from about 0.5 nm (about a monolayer) to about 5 nm. Preferably, the modified surface ranges from about 1 nm to 3 nm thick.

When using the third embodiment of the present invention, the organosulfur surface thickness, after any orientation processing, ranges from about 0.1 µm to 10 µm. The surface can be continuous or discontinuous.

Metallic Layer

Metals useful for the present invention depend on the material properties, (e.g., electrical conductivity) desired for resulting metallic film. Nonlimiting examples of metals include chromium, titanium, nickel, copper, tin, indium, gold, and silver, and alloys of them, with silver preferred for its optimal conductivity. The metal is evaporated in a chamber at low pressures and deposited to react with the sulfur-reactive surface to form metal-sulfur bonds, coordination bonds, or both. Preferably when silver is used, XPS (ESCA) shows the formation of a silver-sulfide bond.

The metallic layer can have any thickness acceptable to the ultimate usage.

For use as conductors in biomedical electrodes used for defibrillation, tissue pacing stimulation, or cardioversion where electrical signals are delivered to mammals, the thickness of the metallic layer ranges from about 100 nm to about 650 nm and preferably ranges from about 300 nm to about 500 nm. For use as conductors in biomedical electrodes used for diagnostic or monitoring procedures where electrical signals are received from mammals, the thickness ranges from about 50 nm to about 300 nm and preferably ranges from 100 nm to about 250 nm.

For use as window films, the thickness ranges from about 0.5 nm to about 600 nm. Desirably, the thickness ranges from about 2 nm to about 25 nm. Preferably, the thickness ranges from about 10 nm to about 13 nm.

For use as optical reflectors, the thickness ranges from about 10 nm to about 1000 nm. Desirably, the thickness ranges from about 15 nm to about 300 nm. Preferably, the thickness ranges from about 20 nm to about 200 nm.

For use in flex circuitry, the thickness ranges from about 10 nm to about 50 µm. Desirably, the thickness ranges from about 30 nm to about 30 µm. Preferably, the thickness ranges from about 100 nm to about 10 µm.

These thickness ranges are broad in that various applications can utilize metallic layers identified at opposite extremes of the identified ranges.

Optional Metallic Halide Layer

In certain uses, particularly as conductors in biomedical electrodes, an optional metallic halide layer is desirably added to or formed on the exposed surface of the metallic layer. Of the halides useful, chloride is preferred. Preferably, the same metal is used in the metal halide as used for the metallic layer. A metallic halide layer interacts with the metallic layer to depolarize the metallic film following high voltage, high amperage defibrillation of a patient. Biomedical electrodes that are capable of quick defibrillation recovery are strongly desired by health care practitioners.

For use as conductors in biomedical electrodes used for defibrillation or stimulation purposes, the thickness of the metallic halide layer ranges from about 100 nm to about 900 nm and preferably from about 500 nm to about 700 nm. For use as conductor in biomedical electrodes used for diagnostic or monitoring purposes, the thickness ranges from about 5 nm (to provide a discontinuous layer) to about 300 nm and preferably 80 nm to 150 nm.

Method of Preparing Sulfur-reactive Surface

In the first embodiment of the present invention, the organic polymer is mixed either before or during polymerization with a sulfur-containing compound such as barium sulfate. Commercially available polyester films have been described above and are especially useful to avoid substrate preparation.

In the second embodiment of the present invention, the sulfur-reactive surface comprises an organosulfur surface.

In the third embodiment of the present invention, the sulfonated surface is prepared according to the techniques described above.

In the preferred second embodiment, the organosulfur surface is prepared by the exposure of organic polymer substrate surface(s) to a vacuum glow discharge or plasma. The gas in which this plasma is created is a sulfur-containing compound, preferably hydrogen sulfide.

Presently preferred reaction conditions for plasma reaction of the sulfur-containing compound are a voltage of about 4–10 kV, an amperage of about 0.04–0.08 A/m width of substrate being treated at 0.15 m/sec, a gas flow ranging from about 70 to about 700 sccm (0.08 to about 0.75 g/m$^2$ of substrate being treated), and a line speed of about 10 to 300 mm/sec. Also for plasma reaction, electrode to substrate spacing is about 10–30 mm, and a chamber pressure is from about 0.7 Pa to 12 Pa for the range of electrode spacings. Also chamber pressure of $O_2$ and $H_2O$ should be minimal and preferably less than $1\times10^{-2}$ Pa. The electrodes are tubular and can be made from stainless steel, or preferably titanium, and are cooled by using airflows or water through tubular structure of the electrodes.

The plasma-induced reaction of the sulfur-containing gas to the substrate surface results in the formation of an organosulfur surface on the substrate. XPS (ESCA) analysis reveals that covalent organosulfur bonds are formed at the surface of the organic polymer.

This organosulfur surface is a priming surface for vapor deposition of the metallic layer.

Method of Preparing Metallic Layer

The metallic layer is formed by evaporative deposition in vacuum of a metal on the sulfur-reactive, and preferably organosulfur, surface of the substrate. Nonlimiting evaporation techniques known to those skilled in the art include heating methods, (e.g., resistive, inductive, and electron beams,) and other physical vapor deposition techniques (e.g., sputtering).

Chamber pressure of $O_2$ and $H_2O$ used in metal deposition depends on the metal selected for vapor deposition due to the tendency of the metal to oxidize. When the metal is silver, the pressure of $O_2$ and $H_2O$ can be up to about $7\times10^{-2}$ Pa.

Method of Preparing Optional Metallic Halide Layer

The optional metallic halide layer can be formed directly from the metallic layer or can be a separate deposition step. When formed in situ, nonlimiting techniques include chemical or electrochemical oxidative chlorination.

Nonlimiting deposition techniques include evaporation in a vacuum using resistive or inductive heating techniques; or solution deposition from aqueous solutions of metallic halides, such as silver chloride.

With multiple layering techniques described, it is possible to combine the method steps into a single pass within a vacuum chamber, such that in a preferred embodiment, hydrogen sulfide treatment, and silver and silver chloride deposition can be sequentially performed on the surface of an organic polymer substrate. Preferably, this organic polymer substrate has been previously prepared with a flashlamp treatment according to the method described above.

Usefulness of the Invention

Figure 1:
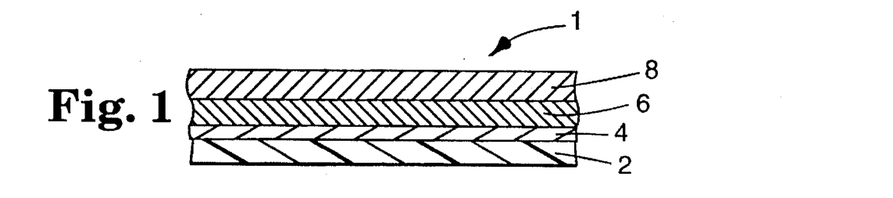
FIG. 1 is a cross-sectional view of a metallic film of the present invention.

FIG. 1 shows a metallic film 1 of the present invention. The substrate 2 has an sulfur-reactive surface 4, (preferably an organosulfur surface) formed thereon, to which a metallic layer 6 is deposited. Optionally as shown, a metallic halide layer 8 is deposited on the metallic layer 6.

Biomedical Electrodes

Biomedical electrodes employing metallic films of the present invention as biomedical electrical conductors are useful for diagnostic or monitoring purposes, for transcutaneous electrical nerve stimulation (TENS) purposes, defibrillation, cardioversion, tissue pacing stimulation, or as a electrical dispersive plate for electrosurgery. In its most basic form, a biomedical electrode is a transducer that converts electrical current to ionic current or vice versa. Minimally, the electrode comprises an ionically conductive medium contacting skin and a means for electrical communication interacting between the ionically conductive medium and biomedical equipment.

Figures 2, 3:
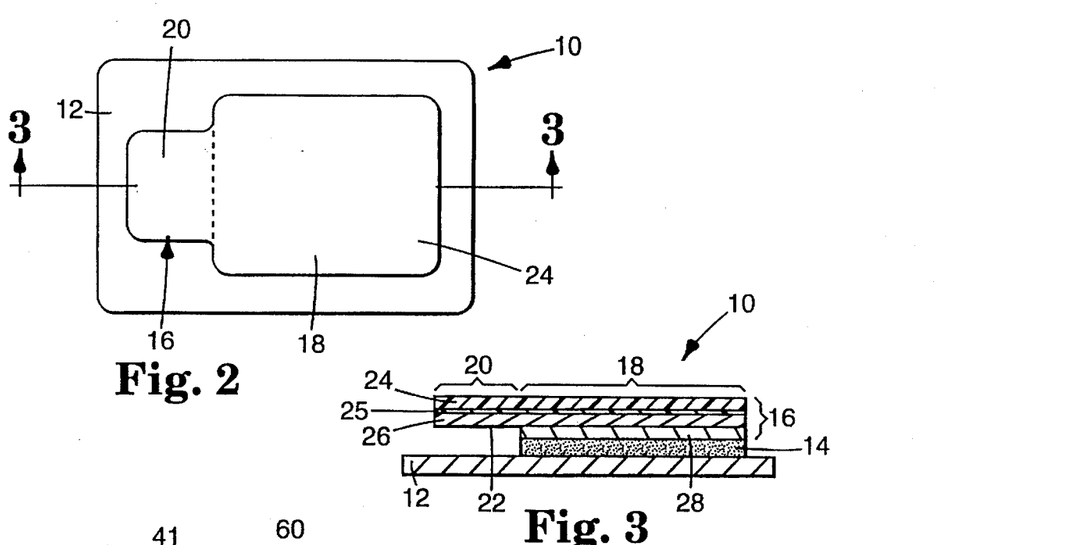
FIG. 2 is a top plan view of a biomedical electrode containing a biomedical electrical conductor of the present invention, used for diagnosis of heart conditions of a mammalian patient.
FIG. 3 is a cross-sectional view of the biomedical electrode of FIG. 2.

FIGS. 2 and 3 show either a disposable diagnostic electrocardiogram (ECG or EKG) electrode 10 or a TENS electrode 10 on a release liner 12. Electrode 10 includes a field 14 of a biocompatible and adhesive ionically conductive medium for contacting skin of a patient upon removal of protective release liner 12. Electrode 10 includes means for electrical communication of the present invention comprising a biomedical electrical conductor 16 having a conductive interface portion 18 contacting field 14 of ionically conductive medium and a tab portion 20 not contacting field 14 of ionically conductive medium for mechanical and electrical contact with electrical equipment (not shown). The tab portion 20 can be arcuately slit (not shown) in an arc of about 120° to about 270° having a radius of about 2 mm to about 5 mm in an internal area of the tab for more assured connection with gripping extension of the electrode clip.

Conductor 16 is shown in a multi-layered construction (similar to that shown in FIG. 1) of a nonconductive, flexible polymeric film substrate 24 having an sulfur-reactive surface 25, a metallic layer 26 deposited on and interacting with the surface 25, and an optional metallic halide layer 28. The conductive interface portion 18 of member 16 comprises a metallic layer 26 deposited on an sulfur-reactive surface 25 on at least the side of polymeric film substrate 24 facing field 14 of conductive medium and the optional metallic halide layer 28 coated on the metallic layer 26 and contacting field 14. Because depolarizing is not needed for the mechanical and electrical contact with electrical equipment, optional metallic halide layer 28 does not need to extend to tab portion 20.

It is foreseen that a typical EKG conductor member 16 be thin and flexible. Polymeric film substrate 24 typically has a thickness ranging from about 20 µm to about 150 µm, and preferably has a thickness of about 75–100 µm.

When used for diagnostic, monitoring, or TENS purposes, metallic layer 26, as a vapor deposited layer, has a thickness ranging from about 80 nm to about 100 nm. When used for defibrillation, tissue pacing stimulation, or cardioversion, metallic layer 26 has a thickness from about 100 nm to about 300 nm, and preferably has a thickness of about 200 nm to achieve at least 50 defibrillation pulses.

When used for diagnostics, monitoring, or TENS purposes, optional metallic halide layer 28, when vapor deposited, has a thickness ranging from about 100 nm to about 350 nm, and preferably a thickness of about 200 nm. When used for defibrillation, tissue pacing stimulation, or cardioversion, optional metallic halide layer 28 has a thickness from about 500 nm to about 700 nm and preferably about 600 nm.

Presently preferred for polymeric film substrate 24 are polyester films such as "Scotchpar" commercially available from Minnesota Mining and Manufacturing Company of St. Paul, Minn. or "Melinex" ICI 329, or ICI 339 film from ICI Americas of Hopewell, Va.

Presently preferred for metallic layer 26 is vapor deposited silver.

To enhance mechanical contact between an electrode clip (not shown) and tab portion 20 of conductor member 16, an adhesively-backed polyethylene tape can be applied to tab portion 20 on the side opposite side 22 having the electrically conductive layer 26. A surgical tape commercially available from 3M Company as "Blenderm" tape can be employed for this purpose.

For the conductive medium 14, ionically-conductive gels and adhesives are used. Nonlimiting examples of ionically-conductive pressure sensitive adhesive compositions are solid state conductive polymer compositions disclosed in U.S. Pat. Nos. 4,524,087; 4,539,996; 4,554,924; and 4,848,353 (all Engel); EPO Publication 0 322 098 (Duan); copending, coassigned United U.S. patent application Ser. No. 07/792,957 (Uy et al.), the disclosures of which are incorporated by reference; and adhesives disclosed in U.S. Pat. No. RE31,454 (Hymes); U.S. Pat. No. 4,391,278 (Cahalan); U.S. Pat. No. 4,699,146 and U.S. Pat. No. 4,750,482 (both Sieverding).

Another type of diagnostic procedure which can employ a biomedical electrode of the present invention is the longer term monitoring of electrical wave patterns of the heart of a patient to detect patterns of abnormality. A preferred biomedical electrode structure is disclosed in U.S. Pat. No. 5,012,810 (Strand et al.) which is incorporated by reference. The metallic film of the present invention can be used as the conductor member in any of the embodiments shown therein. Preferably, the metallic film of the present invention is used as the biomedical electrical conductor in the biomedical electrode of the embodiment shown in FIGS. 2, 3, and 4 of U.S. Pat. No. 5,012,810.

Figure 4:
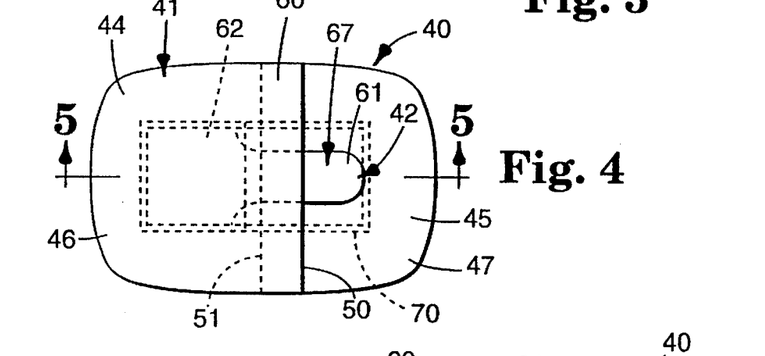
FIG. 4 is a perspective view of a monitoring biomedical electrode containing a biomedical electrical conductor of the present invention, used for longer term diagnosis of heart conditions.
Figure 5:
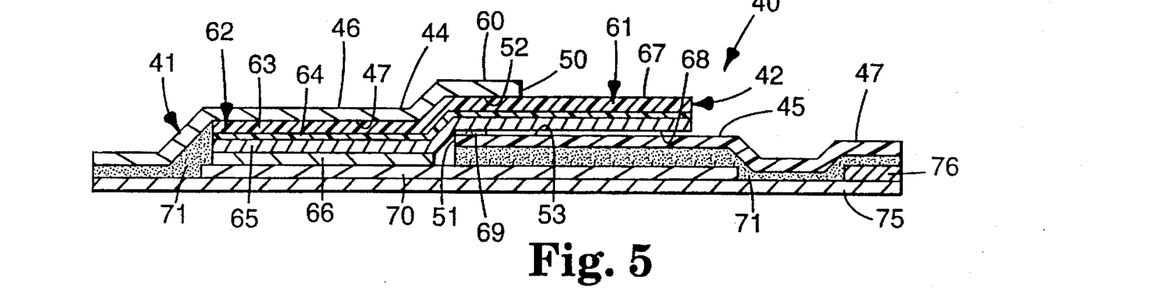
FIG. 5 is a cross-sectional view of the monitoring biomedical electrode of FIG. 4.

FIGS. 4 and 5 substantially correspond to FIGS. 2 and 3, respectively, of U.S. Pat. No. 5,012,810. Electrode 40 includes an insulator construction 41, and a conductor member 42.

The insulator construction 41 includes first and second sections 44 and 45 which, together, define opposite sides 46 and 47 of the insulator construction 41. As seen in FIG. 5, each section 44 and 45 includes an elongate edge portion 50 and 51, respectively. The edge portions 50 and 51 each include a border portion 52 and 53, respectively, which comprise a peripheral portion of each section 44 and 45, respectively, and extending along edges 50 and 51, respectively. In that manner, sections 44 and 45 are oriented to extend substantially parallel to one another, with edge portions 50 and 51 overlapping one another such that border portions 52 and 53 overlap. A seam 60 is created between edge portions 50 and 51. "Substantially parallel" does not mean that the sections 44 and 45 are necessarily precisely parallel. They may be out of precise coplanar alignment due, for example, to the thickness of the conductor member 42.

Conductor member 42 is substantially similar to biomedical electrical conductor 16 described above, having a tab portion 61 corresponding to tab portion 20 described above and a pad portion 62 corresponding to conductive interface portion 18 described above. Like biomedical electrical conductor 16, conductor member 42 is a multi-layered construction of a nonconductive, flexible organic polymer substrate 63 having an organosulfur surface 64, a metallic layer 65 adhered thereto, and, optionally, a metallic halide layer 66.

The pad portion 62 of member 42 comprises the portion of the metallic film facing field 70 of conductive adhesive, optionally with metallic halide layer 66 contacting field 70. Because depolarizing is not needed for the mechanical and electrical contact with electrical equipment, metallic halide layer 66 need not extend to tab portion 61. Optionally, an adhesively-backed polyethylene tape can be applied to tab portion 61 in the same manner as that for the embodiment of FIGS. 1 and 2, in order to enhance mechanical contact.

In general, electrode 40 is constructed such that tab portion 61 of conductor member 42 projects through seam 60 and over a portion of surface or side 46. As a result, as seen in FIGS. 3 and 4, pad portion 62 of conductor member 42 is positioned on one side 47 of insulator construction 41, and the tab portion 61 of conductor member 42 is positioned on an opposite side 46 of insulator construction 41. It will be understood that except where tab portion 61 extends through seam 60, the seam may be sealed by means of an adhesive or the like.

As seen in FIG. 5, lower surface 68 of tab portion 61 is shown adhered in position to section 45, by means of double-stick tape strip 69. That is, adhesion in FIG. 5 between the tab portion 61 and section 45 is by means of adhesive 69 underneath tab portion 61, rather than on top as shown in FIG. 4.

In FIG. 5, a field 70 of conductive adhesive is shown positioned generally underneath conductive member 42. Usually, field 70 of conductive adhesive will be surrounded by a field 71 of skin adhesive also applied to insulator construction 41 the side thereof having pad portion 62 thereon.

In FIG. 5, a layer of release liner 75 is shown positioned against that side of electrode 40 which has skin adhesive 71, conductive adhesive 70 and pad portion 62 thereon. Optionally as shown in FIG. 5, a spacer 76 or tab 76 can be positioned between release liner 75 and a portion of insulator construction 41, to facilitate the separation.

A variety of release liners 75 may be utilized; for example, a liner comprising a polymer such as a polyester or polypropylene material, coated with a silicone release type coating which is readily separable from the skin adhesive and conductive adhesive.

A variety of materials may be utilized to form the sections 44 and 45 of the insulator construction 41. In general, a flexible material is preferred which will be comfortable to the user, and is relatively strong and thin. Preferred materials are polymer foams, especially polyethylene foams, non-woven pads, especially polyester non-wovens, various types of paper, and transparent films. Nonlimiting examples of transparent films include polyester film such as a polyester film commercially available as "Melinex" polyester film from ICI Americas, Hopewell, Va. having a thickness of 0.05 mm and a surgical tape commercially available from 3M Company as "Transpore" unembossed tape.

The most preferred materials are non-woven pads made from melt blown polyurethane fibre, which exhibit exceptional flexibility, stretch recovery and breathability. Melt blown polyurethane materials usable in insulator construction 41 in electrodes according to the present invention are generally described in European Patent Publication 0 341 875 (Meyer) corresponding to U.S. patent application Ser. No. 07/841,890, allowed, incorporated herein by reference.

Preferably the insulator construction has a skin adhesive on its surface contacting the remainder of the electrode 40.

Preferred web materials (melt blown polyurethanes) for use in insulator construction 41 have a web basis weight of about 60–140 g/m$^2$ (preferably about 120 g/m$^2$). Such materials have an appropriate tensile strength and moisture vapor transmission rate. A preferred moisture vapor transmission rate is about 500–3000 grams water/m$^2$/24 hours (preferably 500–1500 grams water/m$^2$/24 hours) when tested according to ASTM E96-80 at 21° C. and 50% relative humidity. An advantage to such materials is that webs formed from them can be made which exhibit good elasticity and stretch recovery. This means that the electrode can stretch well, in all directions, with movement of the subject, without loss of electrode integrity and/or failure of the seal provided by the skin adhesive. Material with a stretch recovery of at least about 85%, in all directions, after stretch of 50% is preferred.

It will be understood that a variety of dimensions may be utilized for the biomedical electrode disclosed herein. Generally an insulator construction of about 3.5–4.5 cm by 5.5–10 cm will be quite suitable for typical foreseen applications. A thickness of about 200 to 600 μm provides for adequate strength and a desired low relief or profile, in typical applications.

It will also be understood that a variety of materials may be utilized as the skin adhesive. Typically, acrylate ester adhesives will be preferred. Acrylate ester copolymer adhesives are particularly preferred. Such material are generally described in U.S. Pat. Nos. 2,973,826; Re 24,906; Re 33,353; 3,389,827; 4,112,213; 4,310,509; 4,323,557; 4,732, 808; 4,917,928; 4,917,929; and European Patent Publication 0 051 935, all incorporated herein by reference.

In particular, an adhesive copolymer having from about 95 to about 97 weight percent iso-octyl acrylate and from about 5 to about 3 percent acrylamide and having an inherent viscosity of 1.1–1.25 dl/g is presently preferred.

Adhesive useful as for adhesive 69 can be any of the acrylate ester adhesives described above in double stick tape form. A presently preferred adhesive is the same adhesive as presently preferred for the skin adhesive except having an inherent viscosity of about 1.3–1.45 dl/g.

For the field 70 of conductive adhesive, conductive adhesives such as those described above as useful for field 14 of conductive medium are preferred. It will be understood that the dimensions of the various layers, and their conformation during association, are shown somewhat exaggerated in FIG. 5, to facilitate an understanding of the construction. In general, an overall substantially flat appearance with only a very minor "s" type bend in the conductive member 42 is accommodated by the arrangement, despite the multi-layered construction of member 42.

Other examples of biomedical electrodes which can use the present invention as biomedical electrical conductors include electrodes disclosed in U.S. Pat. Nos. 4,527,087; 4,539,996; 4,554,924; 4,848,353 (all Engel); U.S. Pat. No. 4,846,185 (Carim); U.S. Pat. No. 4,771,713 (Roberts); U.S. Pat. No. 4,715,382 (Strand); U.S. Pat. No. 5,133,356 (Bryan et al.), the disclosures of which are incorporated by reference herein. Methods of making such electrodes are disclosed in such patents, except that the biomedical electrical conductor of the present invention can be substituted for the various means of electrical communication disclosed in such patents. Among these various electrode constructions is an electrode construction particularly preferred as that shown in FIGS. 4 and 5 of U.S. Pat. No. 4,848,353 (Engel) in which the combination of electrode plate 33 and polymeric backing 34 is replaced by the metallic film 1 of the present invention.

When used for diagnostic EKG procedures, electrodes shown in FIGS. 2 and 3 or those electrodes shown in U.S. Pat. No. 4,539,996 are preferred. When used for monitoring electrocardiogram (ECG) procedures, electrodes disclosed in U.S. Pat. Nos. 4,848,353, 5,012,810 and 5,133,356 are preferred.

In some instances, the biomedical electrical conductor can be an electrically conductive tab extending from the periphery of the biomedical electrodes such as that seen in U.S. Pat. No. 4,848,353 or can be a conductor member extending through a slit or seam in a insulating backing member, such as that seen in U.S. Pat. No. 5,012,810. Otherwise, the means for electrical communication can be an eyelet or other snap-type connector such as that disclosed in U.S. Pat. No. 4,846,185 with the depolarizing layer coated on a graphite coated snap electrode. Alternatively, an electrically conductive tab such as that seen in U.S. Pat. No. 5,012,810 can have an eyelet or other snap-type connector secured thereto.

Figure 6:
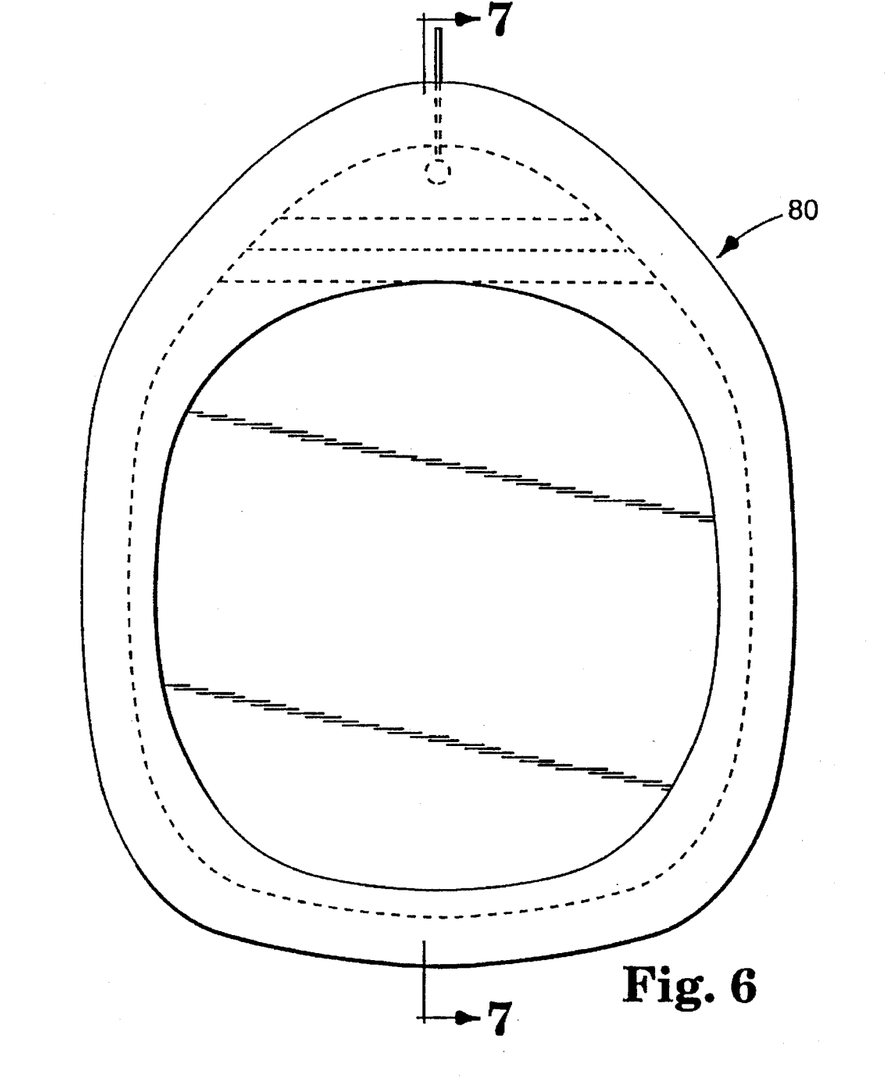
FIG. 6 is a perspective view of a monitoring-defibrillation biomedical electrode used for monitoring of heart conditions and the defibrillation of hearts in emergency conditions with the release liner removed.
Figure 7:
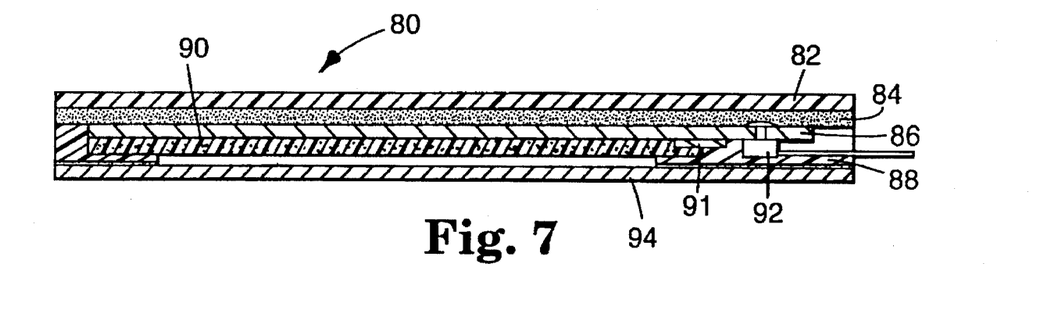
FIG. 7 is a cross-sectional view of the monitoring-defibrillation biomedical electrode of FIG. 6.

Another embodiment of a biomedical electrode is shown in FIGS. 6 and 7. This biomedical electrode is suitable for both monitoring heart activity and for initiating defibrillation, tissue pacing stimulation, and cardioversion procedures. Electrode 80 comprises, in layers, a foam insulating layer 82 having a field 84 of biocompatible pressure sensitive adhesive covering one surface of the layer 82. Within the periphery of adhesive field 84 is adhered a metallic film 86 of the present invention constructed in the same manner as for conductors 16 and 42, previously discussed. At the periphery of metallic film 86 is a non-conductive layer 88 which adheres to field 84 of adhesive and covers the periphery of film 86. Non-conductive layer 88 has an opening in which a field 90 of conductive gel or conductive adhesive adheres to metallic film on the surface at the opening. The interface 91 away from the opening is protected with Blenderm™ tape from 3M Company and the top of the film 86 wherein the connector is to be attached. The opening is where the conductive area is exposed. The non-conductive layer 88 also has biocompatible pressure sensitive adhesive covering one surface, using adhesives described above with respect to the electrodes seen in FIGS. 4 and 5.

The geometric shape of electrode 80 minimizes the presence of any abrupt intersections of edges, such as corners. Each of the components of electrode 80, especially the metallic film 86, is shaped to avoid corners where the edge effect of high voltage, and high wattage electrical power flux to skin can cause arcing and electrical burns. It has been found that the substantially egg shaped metallic film 86 within electrode 80 minimizes arcing when contacting mammalian skin.

Electrical connection from metallic film 86 to electrical instrumentation (not shown) can use a metal-containing or metal-covered post 92 attached to the metal film 86 and insulated from the outside between two foam layers 82 and 88.

It is a feature of this biomedical electrode of FIGS. 6 and 7 that the conductive area of the electrode for tissue pacing stimulating, defibrillation, or cardioversion is limited to that area of the opening as seen in FIGS. 6 and 7, such that arcing and electrical burns caused during tissue pacing stimulation, cardioversion, or defibrillation are minimized at the edge where the field 90 of conductive gel or adhesive contacts metallic film 86. Opening in layer 88 through which field 90 is exposed is smaller in perimeter dimensions than the perimeter edge of field 90 contacting film 86. This diminution of surface area of field 90 is overcome by the edge protection afforded for electrode 80 to minimize arcing and edge burns.

Foam insulating layer 82 can be any non-conductive polymeric foam material useful to those skilled in the art. Nonlimiting examples of such foam materials are high density thin polyethylene foams. Presently preferred for layer 82 is 0.50 mm 8EO Volara polyethylene foam commercially available from Voltek of Lawrence, Mass.

Biocompatible pressure sensitive adhesive useful for field 84 can be any of the skin adhesives identified above. Presently preferred as an adhesive for field 84 is 12 grains of a 91:9 isooctyl acrylate:N-vinyl-2-pyrrolidone copolymer pressure sensitive adhesive or 18 grains of a 94:6 isooctyl acrylate:acrylic acid copolymer tackified with a "Foral" branded colophony acid rosin, such as "Foral AX" or "Foral 85" resins commercially available from Hercules Corporation, present in an amount of from about 35–40 weight percent of the copolymer solids.

Metallic film electrical conductor 86 can employ any combination of the organic polymer substrates, sulfur-reactive surfaces, metallic layers, and optionally, metallic halide layers described above. Presently preferred for metallic film 86 is a 50 to 100 µm thick polyester polymer substrate having a 1 nm thick organosulfur surface, a 450 nm thick vapor deposited silver layer, and a 650 nm thick vapor deposited silver chloride layer.

Non-conductive layer 88 can be any thin polymeric film that adheres well to the field 84 of adhesive. Nonlimiting examples of thin polymeric films include high density polytheylene foam. Presently preferred for layer 88 is the Volara foam identified above.

Conductive gel or adhesive for field 90 can be any of the conductive gels or adhesives previously identified for conductive medium 14 or field 70 of conductive adhesive. Presently preferred for field 90 is an acrylic acid/N-vinyl pyrrolidone copolymer conductive adhesive disclosed in U.S. Pat. No. 4,848,353 containing 3 weight percent of potassium chloride.

Post 92 can be any metallic piece with a mechanical connection compatible with electrical instrumentation, preferably nickel plated.

Nonlimiting examples of electrical instrumentation are defibrillation equipment commercially available from Physio-Control Corporation, Hewlett Packard Corporation, and Marquette Electronics.

A release liner 94, like liner 75 described above, can be used to protect field 90 and foam 88 during storage from premature exposure to the environment.

An advantage of biomedical electrode 80 is that it is acceptably radiolucent and can remain on a patient during radiographic procedures, such as electrophysiology studies and radiotherapy procedures. Such procedures generally use about 75 kV peak, 6 mA. An electrical conductor having a significantly greater thickenss than used here would be radiopaque and would appear in the image produced by the radiographic procedure. X-rays above about 40 KeV, 300 mA do not reveal a biomedical electrode image, notwithstanding the presence of a metallic film of the present invention. The minimization of the amount of radiation absorbing metal via vapor deposition permits acceptable radiolucency.

Window Films

Window films employing metallic films of the present invention are useful for window films which reduce solar radiation, glare, infrared radiation and microwave radiation, or modify color of either reflected or transmitted light. These metallic films are applied to windows for various architectural and energy saving reasons. Metallic films are appropriate for application as window films include silver, copper and alloys of copper such as copper-tin mixtures, indium and gold.

The metallic film are preferably semi-transparent, with luminous transmission ranging from 0.1 to 80%. Desirably, the luminous transmission ranges from 2 to 70%, preferably 5 to 60% in typical applications. The dense, highly adherent metallic films can provide metal films having reduced rates of corrosion, which can be important for this application.

The polymeric substrate used for this application is preferably transparent, scattering a minimum of light, precluding the use of filled films.

Optical Reflectors

Optical reflectors employing metallic films are useful for reflectors for illumination systems and solar energy collectors. For both applications, corrosion stability and adhesion are important properties provided by metallic films of the present invention.

Since reflectors are substantially opaque, (e.g., less than 10% light transmission,) substrates may be filled and thus scatter light, so any one of the three embodiments of the present invention may be used to improve adhesion.

Metallic films of the present invention can be used in solar collectors and reflectors in a manner according to U.S. Pat. Nos. 4,307,150 and 4,645,714 (both Roche), the disclosures of which are incorporated by reference herein.

Flexible Electronic Circuitry

Since flexible electronic circuitry is opaque, optical properties are unimportant. Therefore, substrates may be filled and any one of the three embodiments of the present invention of the metallic films may be used.

Metallic films of the present invention can be used in metal-clad dielectric sheeting in a manner according to U.S. Pat. No. 3,981,691 (Cuneo), the disclosure of which is incorporated by reference herein. Metallic films can also be used in making printed circuitry in a manner according to Canadian Patent 1,011,002 (Cuneo), the disclosure of which is incorporated by reference herein.

Metallic films of the present invention have particular advantage in flexible electronic circuitry due to the low weight, high conductivity requirements in compact electronic products such as notebook computers, watches, facsimile machines, and other electronic products with minimal space between electronically connected modules.

Test Method

Test Method I: Peel test

Two methods are employed to probe the adhesion of the deposited silver coating to the polymeric substrate backing.

Test method A is a simple peel test consisting of applying, with hand pressure, a 20 mm wide by 75 mm long piece of Scotch™ brand Magic Tape (manufactured by the 3M Corporation, St. Paul, Minn.) to the metallic surface, then rapidly remove, with a jerking motion, the tape at a peel angle of approximately 120°. Transfer of any silver from the substrate to the Magic Tape will constitute failure according to this test method.

Test method B employs a specially manufactured test tape. 300 m of 50 μm thick 220 mm wide polyimide filmis coated with a 25% solids solution of UNI-REZ 2645 thermoplastic polyamide adhesive resin (available from Union-Camp Corporation, Wayne, N.J.) in a 70/30 toluene/propanol mixture. Coating conditions are: 150 μm wet coating, web speed 117 mm/sec, oven drying at 68° C. to 90° C. A 25 μm thick (dry) coating is produced. The coated film is converted into rolls of 100 m long 25 mm wide thermoplastic adhesive tape.

Strips of this thermoplastic adhesive tape (150 mm to 200 mm long) are laminated to the vacuum deposited silver surface of the test sample in either cross web or down web direction. The laminating conditions are: nip roll temperature 126° C., nip roll pressure 275 kPa (40 psi), laminating speed 0.5 to 1.5 mm/sec.

After lamination, the test sample is mounted in an Instron Tester Model 1122 (manufactured by Instron Corporation, Canton, Mass.) where the peel force is measured (in grams/25 mm width) at a 90° peel angle and at a speed of 5 mm/sec. In all, but the most severe cases, this procedure results in complete transfer of the silver from the polymeric substrate to the peel tape. The measured peel force (grams/25 mm width) thus provides a reproducible measure of the metal-polymer substrate bond.

Test Method II: Coulometric Determination of AgCl

On a piece of a heavy aluminum foil (150 mm by 150 mm) is extruded a 5 mm thick coating of a solid conductive gel. The top surface of the gel is covered with a polyethylene film to reduce evaporation. Through a slit in this film a given area A of a silver/silver chloride coated conductor film is exposed to the conductive gel surface. A 300 g weight with a basal area of 600 mm$^2$ is placed on top of the conductor film to assure intimate contact with the gel surface. The negative terminal of a precision DC power supply is connected to the end of the conductor film protruding through the slit in the polyethylene cover film. The positive terminal is connected to the aluminum foil assuring a complete circuit. A silver/silver chloride reference electrode is exposed to the gel through a separate slit in the cover film. A strip chart recorder and voltmeter is connected to the end of the conductor film and the reference electrode. When a current (from 3 to 9 mA) is passed through the circuit a sharp voltage offset is observed when all silver chloride on the exposed area of the conductor film has been converted to silver. At this point the current is interrupted and the time recorded. The silver chloride coating thickness, expressed in mC/cm$^2$, can be determined from the time T(sec), The current I(mA), and the area A(cm$^2$):

$$r(mC/cm^2)=[T \times I]/A$$

Test Method III: AAMI Standard Electrical Testing

The AAMI Standards (Association for the Advancement of Medical Instrumentation) for electrical testing of pregelled ECG disposable electrodes can be found in Publication ANSI/AAMI EC12-1983. The Protocol calls for testing performed on electrode pairs placed "back-to-back" with their conductive adhesive/gel columns in contact with each other. Testing according to this protocol was conveniently, and automatically, carried out using a Xtratek model ET-65A ECG Electrode Tester (manufactured by Direct Design,Inc., Lenexa, Kans.).

EXAMPLE 1

In a Research type vacuum coater with a 150 mm wide web drive system was mounted a roll of 50 µm thick polyester film (polyester terephthalate "ScotchPar™" manufactured by 3M Corporation, St Paul, Minn.). The chamber was evacuated to a background pressure of $1.33 \times 10^{-5}$ Pa. A $H_2S$ glow discharge was generated using a water cooled titanium electrode with a ground shield which directed the glow towards the web. A flow of 111 sccm hydrogen sulfide, resulting in a pressure of 2.7 Pa, a DC voltage of 5.0 KV and a current of 0.02 A was used for the glow discharge. The web was treated at a speed of 20 mm/sec in a suspended state. 600 mm further along the web path the treated polyester was coated with a vacuum deposited layer of silver achieving a surface conductivity of 2.5 S (normalized per squared length), an optical transmission of 0.1 to 0.7 percent and a silver coating weight of 0.1 mg/cm². This corresponds to a silver coating thickness of 85 nm. Three additional experiments were performed under varying glow discharge conditions in Table 1:

TABLE 1

| | | $H_2S$ treatment conditions | | | | Silver | |
|---|---|---|---|---|---|---|---|
| exp # | polyester thickness µm | $H_2S$ flow (sccm) | Voltage kV | current A | Sheet conduct. S | Silver weight mg/cm2 | thickness nm |
| 1A | 50 | 111 | 5.0 | 0.02 | 2.5 | 0.1 | 85 |
| 1B | 50 | 111 | 5.0 | 0.02 | 14.5–19 | 0.5 | 443 |
| 1C | 50 | 42 | 3.8 | 0.06 | 7 | 0.16 | — |
| 1D | 50 | 18 | 3.5 | 0.03 | 13 | 0.58 | — |

The adhesion of the silver to the substrate was tested for samples 1A to 1D using test method A as described above. Samples 1A through 1C passed this test, whereas 1D displayed occasional adhesion failure. A sample prepared as outlined above for 1A, but without the $H_2S$ glow discharge treatment, consistently failed the silver adhesion test according to test method A.

EXAMPLE 2

A sample was prepared in similar fashion as example 1, except the silver coating had a thickness of approx. 1 nanometer. The surface of this sample was analyzed using XPS (ESCA). An XPS survey spectrum was recorded of the film surface and, from this spectrum, the following relative surface elemental composition was calculated:

| Atomic % concentration | | | | |
|---|---|---|---|---|
| C | O | Ag | S | Si |
| 59 | 18 | 11 | 4.8 | 7.5 |

The analysis showed the presence of Ag, S, and Si in addition to the base polyester (C, O). The binding energy observed for the $Si(2p^{3/2,1/2})$ photoelectron peak indicated that the silicon was present as a silica type species and thus stemming from the slip agent present on the surface of the PET film. Peak fitting the $S(2p^{3/2,1/2})$ photoelectron spectrum showed two distinct types of sulfur present:

| $S(2p^{3/2})$ Binding energy (eV) | Peak Assignment | % of Total Sulfur |
|---|---|---|
| 161.75 | $Ag_2S$ | 57% |
| 163.62 | Ag-S-PET | 43% |

This analysis demonstrated the presence of "organic" sulfur covalently bound to both the silver coating and the PET film. The strong presence of the $C(1s^{1/2})$ peak in the spectrum, evidence of the PET surface itself, suggested that the "organic sulfur" containing layer was thinner than the ESCA analysis depth (~8 nm)

EXAMPLE 3

Samples were prepared as described in example 1 using 150 mm wide 100 µm thick PET (ScotchPar™). The conditions of the $H_2S$ treatment were varied, and the resulting adhesion of the silver layer measured using peel test method B. The results are indicated in the table 2:

TABLE 2

| | $H_2S$ Primer Condition | | | | | Cross Web Peel | Down web Peel |
|---|---|---|---|---|---|---|---|
| Exp. # | $H_2S$ flow (sccm) | Voltage kV | Current A | Web Temp. °C. | web Speed mm/sec | force grams/ 25 mm | force grams/ 25 mm |
| 3A | 100 | 6.6 | 0.045 | 40 | 12.5 | 102 | — |
| 3B | 100 | 7.1 | 0.045 | 66 | 12.5 | 132 | — |
| 3C | 85 | 7.1 | 0.020 | 46 | 12.5 | 198 | 202 |
| 3D | 85 | 7.1 | 0.020 | 51 | 12.5 | 195 | 197 |
| 3E | 85 | 7.1 | 0.020 | 56 | 8.0 | 142 | 188 |
| 3F | 75 | 7.1 | 0.015 | 53 | 10.0 | 186 | 167 |
| 3G | 85 | 7.1 | 0.030 | 53 | 17.5 | 212 | 215 |
| 3H | No $H_2S$ treatment (control) | | | | | 59 | 47 |

EXAMPLE 4

Several pieces of material 1D from Example 1 were subjected to the following treatment in order to produce a AgCl surface:

a) A 1% bleach solution (Hi-lex commercial household bleach) was coated on the surface with a #6 Meier bar, followed by overnight drying at ambient conditions.

b) A 2% aqueous $NaClO_2$ solution was coated on the silver surface with a #6 Meier bar. After 5 min at ambient conditions the coating was rinsed with water and air dried.

c) A Ag/AgCl ink solution (Ercon R-300 commercially available from Ercon of Waltham, Mass.), at 50% dilution, was coated on the surface with a #6 Meier bar followed by overnight drying at ambient conditions.

d) A 0.5% AgCl in aqueous ammonium hydroxide was coated on the surface with a #6 Meier bar, dried at ambient conditions for 5 min., then followed by a water rinse and air drying.

e) A sample was dipped into a 5% bleach solution for 60 sec., removed, rinsed with water, and air dried.

Following the chloriding step, samples a) through e) were laminated with 0.625 mm thick conductive adhesive ("AA- NVP") (produced according to Example 7 of U.S. Pat. No. 4,848,353 and having the following ingredients with the following weight percents: acrylic acid (9.5); N-vinyl-2-pyrrolidone (9.5); glycerin (51.58); water (25.5); benzildimethylketal (0.7); triethylene glycol bismethacrylate (0.09); potassium chloride (1.0); NaOH (2.64); and guar gum (0.12)) The laminates were then converted into diagnostic electrodes similar to those shown in FIG. 2 with a 20 mm by 25 mm conductive adhesive area, and a 20 mm by 10 mm connector tab. The electrical properties of the samples were tested according to the AAMI Standards protocol. All samples passed this test protocol immediately after conversion into electrodes. Electrodes made from sample a) showed silver delamination after the AAMI test.

Electrodes made from sample e) were further subjected to accelerated aging for 6 weeks within a sealed foil bag placed in a constant temperature oven kept at 58° C. After this period, the aged electrodes still passed the AAMI standards test.

EXAMPLE 5

A 100 mm by 200 mm sheet of silver coated PET film manufactured similarly to described for 1B in example 1, (100 µm thick, 8–10 S sheet conductance) was submerged in an aqueous solution of sodium chloride (4%) and the silver surface electrolytically chlorided employing a current density of 2.75 mA/cm$^2$ until a thickness of 48 mC/cm$^2$, determined by test method II. The Ag/AgCl conductor film was laminated with conductive adhesive (as used in Example 4 above, 0.625 mm thick) and converted into electrodes as described in example 4. The electrodes were packaged in a sealed foil bag and subjected to accelerated aging in an constant temperature oven kept a 58° C.

At various time intervals electrodes were removed from the oven and tested according to the AAMI standards. The electrodes consistently passed this testing. The study was discontinued after 15 weeks of aging.

EXAMPLE 6

A silver coated PET film (150 mm wide, 100 µm thick, 6–9 S sheet conductance) was prepared as described above in example 1 for sample 1B. After silver deposition, the sample was again placed in the vacuum coater, and a layer of silver chloride was deposited on top of the silver coating, by resistively heating a sample of AgCl (commercially available from D. F. Goldsmith Chemicals, Evanston, Ill.) in a quartz boat, using a graphite heater with a boat-to-web distance of 155 mm.

The thickness of the AgCl layer was monitored during deposition using quartz crystal oscillators, and measured after deposition to be 100 mC/cm$^2$ by coulometry (test method II.), or 268 nanometers by ellipsometry. A part of the Ag/AgCl coated film was laminated with 0.625 mm thick conductive adhesive (as used in Example 4 above) and converted into diagnostic type electrodes similar to those shown in FIG. 2 with a 20 mm by 20 mm conductive adhesive area and a 15 mm by 10 mm connector tab. Another part of the Ag/AgCl coated conductor film was further coated with a 200 µm thick layer of conductive adhesive ("Solid State") (prepared according to Example 10 of U.S. patent application Ser. No. 07/792,957 Uy et al.) and converted into diagnostic type electrodes as above.

Both sets of diagnostic electrodes were tested on a panel of 12 healthy volunteers (6 male and 6 female). High quality 12 lead diagnostic ECG recordings were obtained from each set.

The electrodes were further subjected to accelerated aging conditions, and their performance monitored through AAMI standards testing. The results are indicated in the table 3:

TABLE 3

| Conductive Adhesive | Accelerated aging conditions, time after which the AAMI standards are surpassed | | |
|---|---|---|---|
| | 49° C. (120° F.) | 57° C. (135° F.) | 66° C. (150° F.) |
| AA-NVP | Pass 10 weeks | Pass 10 weeks | Pass 6 weeks |
| Solid State | Pass 10 weeks | Pass 10 weeks | Pass 5 weeks |

No silver delamination was observed after aging of any of these samples.

EXAMPLE 7

Under conditions similar to example 1A a sample of 100 µm thick polyester was vapor coated with 0.6 mg/cm$^2$ silver to produce a sheet conductance of 20 S (sample 7A).

An additional sample of 100 µm thick polyester film was coated with 0.45 mg/cm$^2$ silver to produce a sheet conductance of 15 S, then, under conditions similar to example 6, further coated with a layer of silver chloride (sample 7B). The thickness of the silver chloride layer was determined coulometrically using test method II to be 200 mC/cm$^2$. The silver chloride layer showed good adhesion to the underlying silver coating.

Samples 7A and 7B were laminated with 0.625 mm thick conductive adhesive (as used in Example 4 above) and converted into defibrillation electrodes similar to those shown in FIG. 6 with an exposed conductive adhesive area of approximately 90 cm$^2$. Electrode pairs were laminated with the adhesive surfaces together and connected in series with a 50 ohms resistor to a Physio-Control Lifepak 9 defibrillator (manufactured by Physio-Control Corp. of Redmond Wash.). A series of 360 joules pulses were passed through the pairs. Electrodes made from sample 7A did sustain more than 70 pulses without electrical or physical deterioration. Electrodes made from sample 7B did show non polarizability for the first 45 pulses and electrical and physical deterioration (arcing) after approximately 50 to 55 pulses.

Electrodes made from both sample 7A, and sample 7B, were X-rayed and found to be substantially transparent at energy levels above 40 keV.

EXAMPLE 8

A commercial vacuum coater, divided into three operational segments, and equipped to handle a 400 mm wide web, was modified to include a H$_2$S plasma system in the first segment. The plasma system consisted of a stainless steel tubular electrode, air cooled, with a minibox isolating the plasma system from its surrounding. In the second segment, an inductively heated boat for silver metal evaporation was mounted.

Within this system 100 meters of 400 mm wide 75 µm thick PET (ScotchPar™) were treated at 100 mm/sec using 300 sccm $H_2S$, 7 kV and 0.04A, and coated with silver to provide a sheet conductance of 20 S, measured in the vacuum system, in a non-contact, on-line method using a Delcom Instrument 717B (available from the Delcom Corporation, St Paul Park, Minn.). The adhesion of the silver coating was monitored at time $T_o$, and each week for the following five weeks, using the Adhesion Test Method IIB. Table 4 shows the results.

TABLE 4

| Time of test | Cross Web Peel force g/25 mm | Downweb Peel force g/25 mm |
|---|---|---|
| T° | 175 | 175 |
| 1 week | 175 | 175 |
| 2 weeks | 175 | 175 |
| 3 weeks | 175 | 175 |
| 4 weeks | 175 | 175 |
| 5 weeks | 175 | 175 |

EXAMPLE 9

The commercial vacuum coater described in example 8 was further modified to include a resistively heated quartz boat for silver chloride evaporation allowing complete formation of the silver/silver chloride conductor film in a single pass. The system was tested during 2 coating runs each producing approximately 100 meters of material. To provide samples for determining the silver adhesion, a short leader of silver coated substrate was initially recovered at each run before the silver chloride deposition was commenced. Table 5 shows the results.

TABLE 5

| Exp. # | Web Speed mm/sec | Conductance S Ag layer | Silver Adhesion (g/25 mm) cross web | Silver Adhesion (g/25 mm) down web | AgCl (mC/cm²) |
|---|---|---|---|---|---|
| 9A | 150 | 10 | 160 | 160 | 200 |
| 9B | 125 | 20 | 200 | 200–240 | 280 |

EXAMPLE 10:

Under conditions similar to described in Example 8, the following examples were carried out using different polymeric backings and a deposition rate producing a silver conductance of 20 S at a coating speed of 100 mm/sec. Table 6 shows the results.

TABLE 6

| Exp # | Substrate | $H_2S$ Treatment | Peel Force (g/25 mm) Cross web | Peel Force (g/25 mm) Down Web |
|---|---|---|---|---|
| 10A | Scotchpar ™, flashlamp treated film[1] | Yes | 325–475 | 350–450 |
| 10B | -same- | No | 100–200 | 80–100 |
| 10C | Scotchpar ™ film[2] | Yes | 180–200 | 175–225 |
| 10D | -same- | No | 85–120 | 80–100 |
| 10E | ICI 339 film[3] | Yes | 700–850 | 400–800 |

TABLE 6-continued

| Exp # | Substrate | $H_2S$ Treatment | Peel Force (g/25 mm) Cross web | Peel Force (g/25 mm) Down Web |
|---|---|---|---|---|
| 10F | -same- | No | 1000 | 950–1050 |
| 10G | Hoechst film[4] | No | 250–450 | 300–350 |

[1]Scotchpar ™ film commercially available from 3M flashlamp treated according to U.S. Pat. Nos. 4,822,451 and 4,879,176.
[2]Scotchpar ™ film commercially available from 3M.
[3]ICI 3319 commercially available from ACI Americas.
[4]Hoechst SA 3000 sulfonated film commercially available from Hoechst Chemicals.

Without being limited to the embodiments described, the scope of the present invention is found in the following claims.

What is claimed is:

1. A method for forming a metallic film, comprising the steps of:

(a) creating a sulfur-reactive surface on an organic polymer substrate, and (b) depositing metal on the sulfur-reactive surface causing a sulfur-metal interaction to form a metallic layer.

2. The method according to claim 1, wherein the creating step comprises mixing a sulfur-containing compound into the organic polymer such that at least some of the sulfur-containing compound forms the sulfur-reactive surface.

3. The method according to claim 1, wherein the creating step comprises plasma-induced reaction of a sulfur-containing compound vapor with a surface of the organic polymer.

4. The method according to claim 3, further comprising prior to the creating step, the step of pre-treating the surface of the organic polymer to render the surface quasi-amorphous.

5. The method according to claim 3, wherein the sulfur-containing gas or vapor comprises alkyl mercaptans, hydroxyalkyl mercaptans, hydrogen sulfide, alkyl sulfides, carbon disulfide, or other sulfide gases.

6. The method according to claim 5, wherein the sulfur-containing gas comprises hydrogen sulfide gas.

7. The method according to claim 1, wherein the creating step comprises flood coating an aqueous dispersion of a sulfonated compound on to the organic polymer substrate.

8. The method according to claim 1, further after the depositing step, the step of forming a metal halide layer on the metallic layer.

9. The method according to claim 8, wherein the forming step comprises vapor deposition of the metal halide, solution deposition of metal halide, conversion of the metal to a metal halide by chemical oxidation, or conversion of the metal to a metal halide by electrochemical oxidation.

10. The method according to claim 1, wherein the metallic layer is continuous.

11. The method according to claim 1, wherein the metallic layer is discontinuous.

* * * * *